(12) United States Patent
Wolf et al.

(10) Patent No.: US 9,000,152 B2
(45) Date of Patent: Apr. 7, 2015

(54) PROCESS FOR MANUFACTURING TRIAZINON-BENZOXAZINONES

(71) Applicants: Bernd Wolf, Niederkirchen (DE); Volker Maywald, Ludwigshafen (DE); Uwe Josef Vogelbacher, Ludwigshafen (DE); Michael Rack, Eppelheim (DE); Maximilian Dochnahl, Mannheim (DE); Michael Keil, Freinsheim (DE); Timo Frassetto, Mannheim (DE); Joachim Gebhardt, Wachenheim (DE)

(72) Inventors: Bernd Wolf, Niederkirchen (DE); Volker Maywald, Ludwigshafen (DE); Uwe Josef Vogelbacher, Ludwigshafen (DE); Michael Rack, Eppelheim (DE); Maximilian Dochnahl, Mannheim (DE); Michael Keil, Freinsheim (DE); Timo Frassetto, Mannheim (DE); Joachim Gebhardt, Wachenheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/364,160

(22) PCT Filed: Dec. 20, 2012

(86) PCT No.: PCT/EP2012/076376
§ 371 (c)(1),
(2) Date: Jun. 10, 2014

(87) PCT Pub. No.: WO2013/092858
PCT Pub. Date: Jun. 27, 2013

(65) Prior Publication Data
US 2014/0316131 A1    Oct. 23, 2014

(30) Foreign Application Priority Data
Dec. 23, 2011  (EP) .................................. 11195506

(51) Int. Cl.
C07D 413/14  (2006.01)
A01N 43/84  (2006.01)
C07D 413/04  (2006.01)

(52) U.S. Cl.
CPC .............. C07D 413/04 (2013.01); A01N 43/84 (2013.01)

(58) Field of Classification Search
USPC ......................................................... 544/105
See application file for complete search history.

(56) References Cited

FOREIGN PATENT DOCUMENTS

WO    WO 2010/145992    12/2010
WO    WO 2011/057935    5/2011

OTHER PUBLICATIONS

International Search Report, PCT/EP2012/076376, search completed Mar. 1, 2013.
International Preliminary Report on Patentability, PCT/EP2012/076376, report issued Jun. 24, 2014.

*Primary Examiner* — Kahsay Habte
(74) *Attorney, Agent, or Firm* — Brinks Gilson & Lione

(57) ABSTRACT

The present invention relates to a process for manufacturing triazinon-benzoxazinones of formula (I),

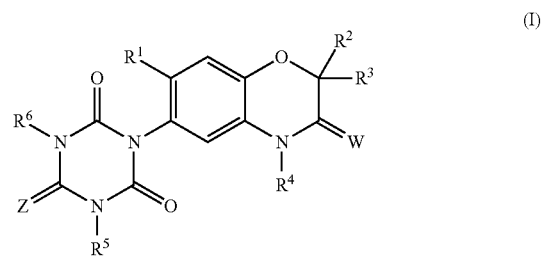

by reacting amino-benzoxazinones of formula (II) with 1,1'-carbonyldiimidazole (CDI) and a (thio)urea compound of formula (III); wherein the variables are defined according to the description.

10 Claims, No Drawings

PROCESS FOR MANUFACTURING TRIAZINON-BENZOXAZINONES

This application is a National Stage application of International Application No. PCT/EP2012/076376, filed Dec. 20, 2012, the entire contents of which is hereby incorporated herein by reference. This application also claims priority under 35 U.S.C. §119 to EP Patent Application No. 11195506.8, filed Dec. 23, 2011, the entire contents of which is hereby incorporated herein by reference.

The invention relates to a process for manufacturing triazinon-benzoxazinones and the use of amino-benzoxazinones in manufacturing triazinon-benzoxazinones.

WO 2010/145992 discloses a synthesis of herbicidal benzoxazinones from amino-benzoxazinones via the corresponding isocyanate. This process involves two steps and requires the use of diphosgene.

Hence, there is still room for improvement, specifically in view of economical and ecological aspects.

One task of the invention is to provide an efficient process for manufacturing triazinon-benzoxazinones that offers an alternative to the use of diphosgene.

It has been found that amino-benzoxazinones of formula (II) can be directly converted into triazinon-benzoxazinones of formula (I) using 1,1'-carbonyldiimidazole (CDI), a (thio) urea compound of formula (III), and optionally a base.

Accordingly, in one aspect of the invention there is provided a process for manufacturing triazinon-benzoxazinones of formula (I),

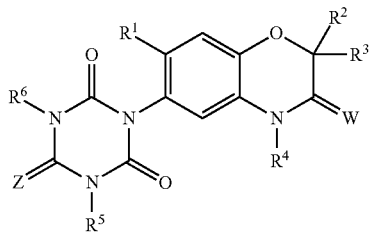

wherein
$R^1$ is H or halogen;
$R^2$ is halogen;
$R^3$ is H or halogen;
$R^4$ is H, $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;
$R^5$ is H, $NH_2$, $C_1$-$C_6$-alkyl or $C_3$-$C_6$-alkynyl;
$R^6$ is H or $C_1$-$C_6$-alkyl;
W is O or S; and
Z is O or S;
wherein
amino-benzoxazinones of formula (II),

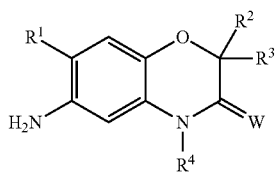

wherein $R^1$, $R^2$, $R^3$, $R^4$ and W are defined as in formula (I); are reacted with 1,1'-carbonyldiimidazole (CDI) and (thio) urea compounds of formula (III),

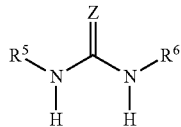

wherein $R^5$, $R^6$ and Z are defined as in formula (I).

In a further aspect of the invention there is provided the use of amino-benzoxazinones of formula (II) in manufacturing triazinon-benzoxazinones of formula (I).

The process according to the invention does not require the synthesis of an additional intermediate. Consequently, it involves only one step starting from the corresponding amino-benzoxazinone. The reduced number of steps leads to shorter synthesis times and lower synthesis costs. Further the use of diphosgene is no longer necessary.

The organic moieties mentioned in the definition of the variables $R^1$ to $R^6$ are—like the term halogen—collective terms for individual enumerations of the individual group members. The term halogen denotes in each case fluorine, chlorine, bromine or iodine. All hydrocarbon chains, i.e. all alkyl, can be straight-chain or branched, the prefix $C_n$-$C_m$ denoting in each case the possible number of carbon atoms in the group.

Examples of such meanings are:

$C_1$-$C_4$-alkyl: for example $CH_3$, $C_2H_5$, n-propyl, and $CH(CH_3)_2$ n-butyl, $CH(CH_3)$—$C_2H_5$, $CH_2$—$CH(CH_3)_2$ and $C(CH_3)_3$;

$C_1$-$C_6$-alkyl and also the $C_1$-$C_6$-alkyl moieties of $C_1$-$C_6$-alkyoxy-$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_4$-haloalkyl: a $C_1$-$C_4$-alkyl radical as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, a $C_1$-$C_3$-haloalkyl radical as mentioned above, and also, for example, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_6$-haloalkyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_3$-$C_6$-cycloalkyl and also the cycloalkyl moieties of $C_3$-$C_6$-cycloalkyl-$C_1$-$C_4$-alkyl: monocyclic saturated hydrocarbons having 3 to 6 ring members, such as cyclopropyl, cyclobutyl, cyclopentyl and cyclohexyl;

$C_3$-$C_6$-alkenyl: for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_3$-$C_6$-haloalkenyl: a $C_3$-$C_6$-alkenyl radical as mentioned above which is partially or fully substituted by fluorine, chlorine, bromine and/or iodine, for example 2-chloroprop-2-en-1-yl, 3-chloroprop-2-en-1-yl, 2,3-dichloroprop-2-en-1-yl, 3,3-dichloroprop-2-en-1-yl, 2,3,3-trichloro-2-en-1-yl, 2,3-dichlorobut-2-en-1-yl, 2-bromoprop-2-en-1-yl, 3-bromoprop-2-en-1-yl, 2,3-dibromoprop-2-en-1-yl, 3,3-dibromoprop-2-en-1-yl, 2,3,3-tribromo-2-en-1-yl or 2,3-dibromobut-2-en-1-yl;

$C_3$-$C_6$-alkynyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_3$-$C_6$-haloalkynyl: a $C_3$-$C_6$-alkynyl radical as mentioned above which is partially or fully substituted by fluorine, chlorine, bromine and/or iodine, for example 1,1-difluoroprop-2-yn-1-yl, 3-chloroprop-2-yn-1-yl, 3-bromoprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_1$-$C_4$-alkoxy: for example methoxy, ethoxy, propoxy, 1-methylethoxy butoxy, 1-methylpropoxy, 2-methylpropoxy and 1,1-dimethylethoxy;

$C_1$-$C_6$-alkoxy: $C_1$-$C_4$-alkoxy as mentioned above, and also, for example, pentoxy, 1-methylbutoxy, 2-methylbutoxy, 3-methoxylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy.

The preferred embodiments of the invention mentioned herein below have to be understood as being preferred either independently from each other or in combination with one another.

According to a preferred embodiment of the invention preference is also given to the preparation of those triazinonbenzoxazinones of formula (I), wherein the variables, either independently of one another or in combination with one another, have the following meanings:

$R^1$ is preferably H or F; particularly preferred H;
   is also preferably halogen, particularly preferred F or Cl, especially preferred F;

$R^2$ is preferably Cl or F, particularly preferred F;

$R^3$ is preferably H, Cl or F, particularly preferred H or F, especially preferred H;
   is also preferably halogen, particularly preferred F or Cl, especially preferred F;

$R^4$ is preferably $C_3$-$C_6$-alkynyl or $C_3$-$C_6$-haloalkynyl, more preferably $C_3$-alkynyl or $C_3$-haloalkynyl, particularly preferred $CH_2C\equiv CH$, $CH_2C\equiv CCl$ or $CH_2C\equiv CBr$;
   is also preferably $C_3$-$C_6$-alkynyl or $C_3$-$C_6$-cycloalkyl-$C_1$-$C_6$-alkyl, particularly preferred propargyl or cyclopropylmethyl;
   is also preferably $C_3$-$C_6$-alkynyl, more preferably $C_3$-alkynyl; particularly preferred $CH_2C\equiv CH$;
   is also preferably $C_3$-$C_6$-haloalkynyl, more preferably $C_3$-haloalkynyl, particularly preferred $CH_2C\equiv CCl$ or $CH_2C\equiv CBr$;

$R^5$ is preferably $NH_2$, $C_1$-$C_6$-alkyl or $C_3$-$C_6$-alkynyl; also preferably H or $C_1$-$C_6$-alkyl; more preferably $C_1$-$C_6$-alkyl; most preferably $C_1$-$C_4$-alkyl; particularly preferred $CH_3$;

$R^6$ is preferably $C_1$-$C_6$-alkyl; more preferably $C_1$-$C_4$-alkyl; most preferably $CH_3$;

W is preferably O,
   is also preferably S;

Z is preferably O,
   is also preferably S.

Particular preference is also given to the preparation of triazinon-benzoxazinones of formula (I.a), which correspond to triazinon-benzoxazinones of formula (I) wherein $R^2$ is F, $R^5$ and $R^6$ are $CH_3$, W is O and Z is S:

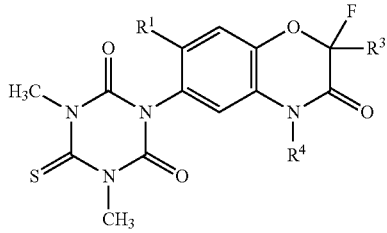

(I.a)

wherein the variables $R^1$, $R^3$ and $R^4$ have the meanings, in particular the preferred meanings, as defined above; most preference to the preparation of triazinon-benzoxazinones of formulae (I.a.1) to (I.a.54) of Table A listed below, in which the variables $R^1$, $R^3$ and $R^4$ together have the meanings given in one row of Table A (triazinon-benzoxazinones of formulae I.a.1 to I.a.54); and where the definitions of the variables $R^1$, $R^3$ and $R^4$ are of particular importance for the process and the compounds according to the invention not only in combination with one another but in each case also on their own:

TABLE A

| No. | $R^1$ | $R^3$ | $R^4$ |
|---|---|---|---|
| I.a.1. | H | H | H |
| I.a.2. | H | H | $CH_3$ |
| I.a.3. | H | H | $C_2H_5$ |
| I.a.4. | H | H | $CH_2$—$C_2H_5$ |
| I.a.5. | H | H | $CH(CH_3)_2$ |
| I.a.6. | H | H | $CH_2$—$CH_2$—$(CH_3)_2$ |
| I.a.7. | H | H | $CH_2$—$CH$=$CH_2$ |
| I.a.8. | H | H | $CH_2C$≡$CH$ |
| I.a.9. | H | H | $CH_2C$≡$C$—Br |
| I.a.10. | H | F | H |
| I.a.11. | H | F | $CH_3$ |
| I.a.12. | H | F | $C_2H_5$ |
| I.a.13. | H | F | $CH_2$—$C_2H_5$ |
| I.a.14. | H | F | $CH(CH_3)_2$ |
| I.a.15. | H | F | $CH_2$—$CH_2$—$(CH_3)_2$ |
| I.a.16. | H | F | $CH_2$—$CH$=$CH_2$ |
| I.a.17. | H | F | $CH_2C$≡$CH$ |
| I.a.18. | H | F | $CH_2C$≡$C$—Br |
| I.a.19. | F | H | H |
| I.a.20. | F | H | $CH_3$ |
| I.a.21. | F | H | $C_2H_5$ |
| I.a.22. | F | H | $CH_2$—$C_2H_5$ |
| I.a.23. | F | H | $CH(CH_3)_2$ |
| I.a.24. | F | H | $CH_2$—$CH_2$—$(CH_3)_2$ |
| I.a.25. | F | H | $CH_2$—$CH$=$CH_2$ |
| I.a.26. | F | H | $CH_2C$≡$CH$ |
| I.a.27. | F | H | $CH_2C$≡$C$—Br |
| I.a.28. | F | F | H |
| I.a.29. | F | F | $CH_3$ |
| I.a.30. | F | F | $C_2H_5$ |
| I.a.31. | F | F | $CH_2$—$C_2H_5$ |
| I.a.32. | F | F | $CH(CH_3)_2$ |
| I.a.33. | F | F | $CH_2$—$CH_2$—$(CH_3)_2$ |
| I.a.34. | F | F | $CH_2$—$CH$=$CH_2$ |
| I.a.35. | F | F | $CH_2C$≡$CH$ |
| I.a.36. | F | F | $CH_2C$≡$C$—Br |
| I.a.37. | Cl | H | H |
| I.a.38. | Cl | H | $CH_3$ |
| I.a.39. | Cl | H | $C_2H_5$ |
| I.a.40. | Cl | H | $CH_2$—$C_2H_5$ |
| I.a.41. | Cl | H | $CH(CH_3)_2$ |
| I.a.42. | Cl | H | $CH_2$—$CH_2$—$(CH_3)_2$ |

TABLE A-continued

| No. | $R^1$ | $R^3$ | $R^4$ |
|---|---|---|---|
| I.a.43. | Cl | H | $CH_2$—$CH$=$CH_2$ |
| I.a.44. | Cl | H | $CH_2C$≡$CH$ |
| I.a.45. | Cl | H | $CH_2C$≡$C$—Br |
| I.a.46. | Cl | F | H |
| I.a.47. | Cl | F | $CH_3$ |
| I.a.48. | Cl | F | $C_2H_5$ |
| I.a.49. | Cl | F | $CH_2$—$C_2H_5$ |
| I.a.50. | Cl | F | $CH(CH_3)_2$ |
| I.a.51. | Cl | F | $CH_2$—$CH_2$—$(CH_3)_2$ |
| I.a.52. | Cl | F | $CH_2$—$CH$=$CH_2$ |
| I.a.53. | Cl | F | $CH_2C$≡$CH$ |
| I.a.54. | Cl | F | $CH_2C$≡$C$—Br |

Very particular preference is given to the preparation of the triazinon-benzoxazinone of formula (I.a.28) as defined above:

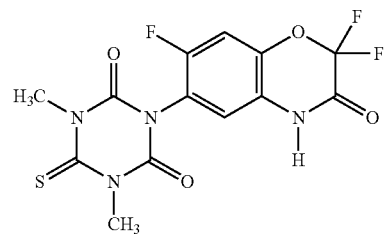

(I.a.28)

Also very particular preference is given to the preparation of the triazinon-benzoxazinone of formula (I.a.35) as defined above:

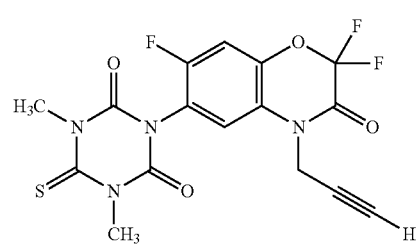

(I.a.35)

With respect to the variables within the compounds of formulae (II) or (III), the particularly preferred embodiments of the compounds of formulae (II) or (III) correspond, either independently of one another or in combination with one another, to those of the variables of $R^1$, $R^2$, $R^3$, $R^4$, $R^5$, $R^6$, W and Z of formula (I).

The amino-benzoxazinones of formula (II) necessary for the process according to the invention can be prepared as described further below.

CDI necessary for the process according to the invention is commercially available.

The (thio)urea compounds of formula (III) necessary for the process according to the invention are commercially available or can be prepared by methods known in the art, see e.g. H. Salkowski, Chem. Ber. 24 (1891) 2724; J. W. Lown, S. M. S. Chaudan, J. Org. Chem. 48 (1983) 507; R. Andreasch, Monatshefte für Chemie 2 (1881) 276.

Preferably CDI is used in excess with regard to the amino-benzoxazinone of formula (II), more preferably at least two equivalents of CDI with regard to the amino-benzoxazinone of formula (II) are used. Particularly preferred the molar ratio of the amino-benzoxazinone of formula (II) to CDI is in the range from 1:2 to 1:5, especially preferred from 1:2.5 to 1:3.5, more preferably 1:3.

In general at least one equivalent of (thio)urea compound of formula (III) with regard to the amino-benzoxazinone of formula (II) is used. Preferably the (thio)urea compound of formula (III) is used in excess with regard to the amino-benzoxazinone of formula (II). The molar ratio of the amino-benzoxazinone of formula (II) to the (thio)urea compound of formula (III) is particularly preferred in the range from 1:1 to 1:2.0, especially preferred from 1:1 to 1:1.5, more preferably from 1:1.1 to 1:1.3.

In one embodiment the reaction of the amino-benzoxazinone of formula (II) with CDI and the (thio)urea compound of formula (III) is carried out in the absence of a base.

In a preferred embodiment the reaction of the amino-benzoxazinone of formula (II) with CDI and the (thio)urea compound of formula (III) is carried out in the presence of a base.

Examples of suitable bases include metal-containing bases and nitrogen-containing bases.

Examples of suitable metal-containing bases are carbonates such as lithium carbonate, sodium carbonate, potassium carbonate, cesium carbonate, magnesium carbonate, calcium carbonate, barium carbonate; hydrogen carbonates such as lithium hydrogen carbonate, sodium hydrogen carbonate, potassium hydrogen carbonate; hydroxides such as lithium hydroxide, sodium hydroxide, potassium hydroxide, magnesium hydroxide, calcium hydroxide, barium hydroxide, aluminum hydroxide; oxides such as lithium oxide, sodium oxide, potassium oxide, magnesium oxide, calcium oxide, barium oxide, iron oxide, silver oxide; hydrides such as lithium hydride, sodium hydride, potassium hydride, calcium hydride; phosphates such as potassium phosphate, calcium phosphate; alkoxides such as sodium, potassium or magnesium alkoxides; and acetates such as sodium acetate or potassium acetate.

Examples of suitable nitrogen-containing bases are ammonia, $C_1$-$C_6$-alkylamines, preferably trialkylamines, for example triethylamine, trimethylamine, N-ethyldiisopropylamine; pyridine, lutidine, collidine, 4-(dimethylamino)pyridine (DMAP), imidazole, 1,8-diazabicyclo[5.4.0]undec-7-ene (DBU) or 1,5-diazabicyclo[4.3.0]non-5-ene (DBN).

Preferred bases are tri-$C_1$-$C_6$-alkylamines, e.g. triethylamine, trimethylamine and N-ethyldiisopropylamine; and imidazole.

Especially preferred bases are tri-$C_1$-$C_6$-alkylamines, more preferrably triethylamine.

The term base as used herein also includes mixtures of two or more, preferably two of the above compounds. Particular preference is given to the use of one base.

Accordingly, in a particularly preferred embodiment the reaction of the amino-benzoxazinone of formula (II) with CDI and the (thio)urea compound of formula (III) is carried out in the presence of one base.

Preferably the molar ratio of the amino-benzoxazinone of formula (II) to the base is in the range from 1:0.5 to 1:2.0, preferably from 1:0.9 to 1:1.2. More preferably the amino-benzoxazinone of formula (II) and the base are used in equimolar amounts.

In another embodiment of the invention the base is used as solvent during the reaction.

The reaction of the amino-benzoxazinone of formula (II) with CDI, the (thio)urea compound of formula (III), and optionally a base can be carried out in a solvent.

Examples of suitable solvents are dipolar aprotic solvents such as N,N-dimethylformamide (DMF), N,N-dimethylacetamide (DMAC), 1-methyl-2-pyrrolidinone (NMP), 1,3-dimethyl-2-imidazolidinone (DMI), N,N'-dimethylpropylene urea (DMPU), dimethyl sulfoxide (DMSO), acetonitrile, acetone, methyl ethyl ketone, methyl butyl ketone, cyclohexanone, sulfolane, nitromethane; esters such as ethyl acetate, butyl acetate; ethers such as dibutylether, tert-butyl methyl ether (TBME), tetrahydrofurane (THF), dioxane; alcohols such as methanol, ethanol, isopropanol, tert-butanol; halogenated hydrocarbons such as chloroform, dichloroethane, carbon tetrachloride; aliphatic hydrocarbons such as hexanes, cyclohexane; aromatic hydrocarbons such as benzene, toluene, cresols, chlorobenzene.

Preferred solvents include ethyl acetate, butyl acetate, tetrahydrofurane or toluene.

More preferred solvents include ethyl acetate, butyl acetate or toluene.

The term solvent as used herein also includes mixtures of two or more of the above compounds.

The reaction of the amino-benzoxazinone of formula (II) with CDI, the (thio)urea compound of formula (III), and optionally a base is generally carried out at a temperature in the range from room temperature to 140° C., preferably from room temperature to 120° C., especially preferred in the range from 70 to 120° C., more preferably in the range from 70 to 100° C.

In a preferred embodiment the amino-benzoxazinone of formula (II) is added to the CDI, the optional base, and preferably a solvent. The mixture is brought to a temperature in the range of from 30 to 80° C., preferably 45 to 65° C., and the (thio)urea compound of formula (III) is added. The mixture is then brought to a temperature in the range of from 70 to 120° C., preferably 70 to 100° C.

The reaction can be carried out at atmospheric pressure, reduced pressure or under elevated pressure, if appropriate under an inert gas, continuously or batchwise.

After completion or partial completion of the reaction, the respective mixture can be worked up by means of standard techniques. Examples thereof include filtration, aqueous work-up, evaporation of solvents and/or other volatile compounds. These methods can also be combined with each other.

In a preferred embodiment the reaction mixture is brought to room temperature and subjected to an acidic aqueous work-up.

The crude product can be purified, e.g. by distillation, crystallization, recrystallization or column chromatography.

In a preferred embodiment, the product is purified by crystallization and/or recrystallization.

The purity of the triazinon-benzoxazinones (I) determined by HPLC is preferably at least 95%, more preferably at least 98%.

The reaction of the amino-benzoxazinone of formula (II) with CDI, the (thio)urea compound of formula (III), and optionally a base may proceed via one or more intermediates of formulae (IVa), (IVb), (IVc), (IVd), (IVe) with "Im" being imidazolyl:

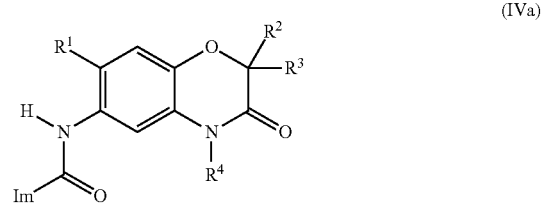
(IVa)

-continued

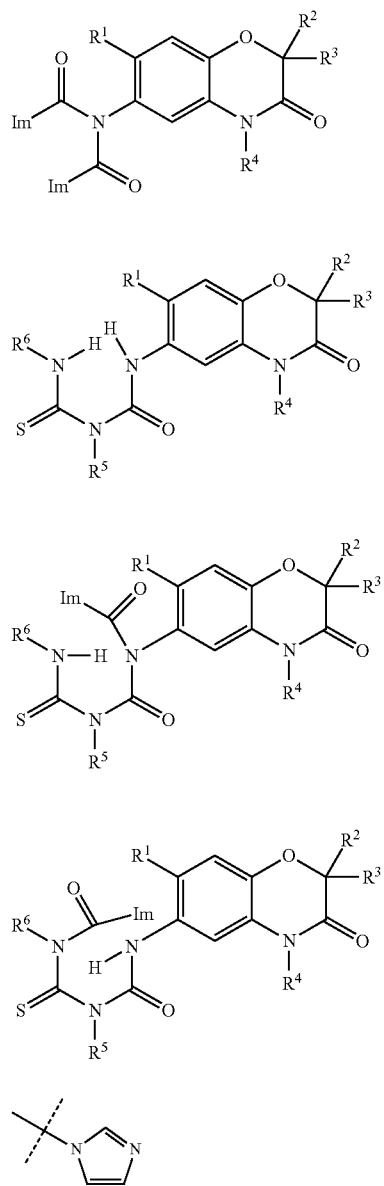

wherein $R^1$, $R^2$, $R^3$, $R^4$, $R^5$ and $R^6$ are defined as above; and $R^5$ and $R^6$ in formulae (IVa), (IVb), (IVc), (IVd), (IVe) are interchangeable.

The amino-benzoxazinones of formula (II) necessary for the process according to the invention can be prepared as follows:

The term "amino-benzoxazinones of formula (II)" combines NH-benzoxazinones of formula (II-1) (corresponding to amino-benzoxazinones of formula (II), wherein $R^4$ is H), and 4-substituted amino-benzoxazinones of formula (II-2) (corresponding to amino-benzoxazinones of formula (II), wherein $R^4$ is $R^\#$).

The 4-substituted amino-benzoxazinones of formula (II-2) (corresponding to amino-benzoxazinones of formula (II) wherein $R^4$ is R#) can be prepared by reacting NH-benzoxazinones of formula (II-1) (corresponding to amino-benzoxazinones of formula (II) wherein $R^4$ is H) with a base and a compound of formula (V), $R^\#L^\#$:

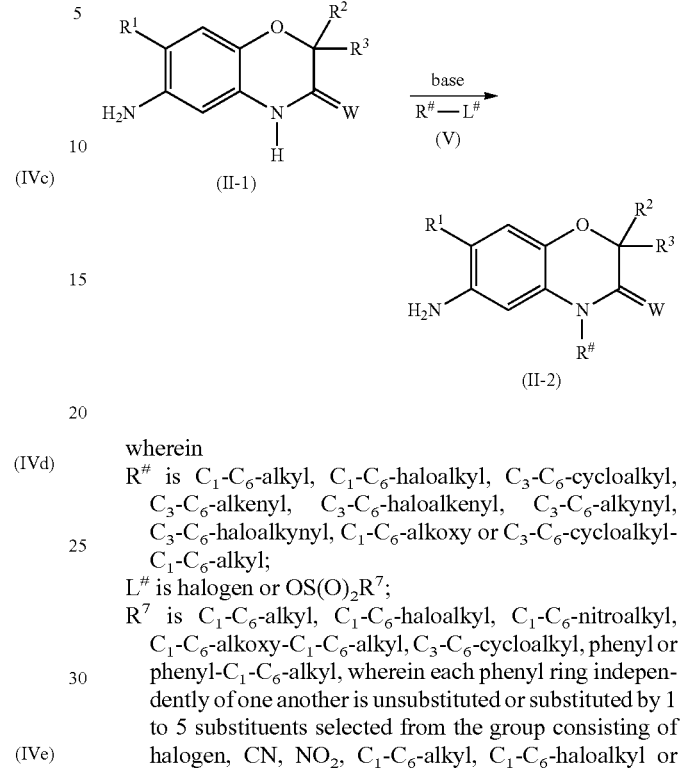

wherein
$R^\#$ is $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;

$L^\#$ is halogen or $OS(O)_2R^7$;

$R^7$ is $C_1$-$C_6$-alkyl, $C_1$-$C_6$-haloalkyl, $C_1$-$C_6$-nitroalkyl, $C_1$-$C_6$-alkoxy-$C_1$-$C_6$-alkyl, $C_3$-$C_6$-cycloalkyl, phenyl or phenyl-$C_1$-$C_6$-alkyl, wherein each phenyl ring independently of one another is unsubstituted or substituted by 1 to 5 substituents selected from the group consisting of halogen, CN, $NO_2$, $C_1$-$C_6$-alkyl, $C_1$-$C_6$-haloalkyl or $C_1$-$C_6$-alkoxy; and $R^1$, $R^2$, $R^3$ and W are defined as in formula (II) above.

The NH-benzoxazinone of formula (II-1) that is converted into the 4-substituted amino-benzoxazinone of formula (II-2) can also be used in the form of a salt, for example in form of its alkali metal or alkaline metal salt, preferably in the form of its lithium, sodium or potassium salt. If a salt of the NH-benzoxazinone of formula (II-1) is used, the addition of a base is not necessary.

The compounds of formula (V), $R^\#$-$L^\#$, necessary for the preparation of the 4-substituted amino-benzoxazinone of formula (II-2), are commercially available, or can be prepared by methods known in the art, e.g. Houben-Weyl 1985, E11-2, p. 1084.

Accordingly, in a further preferred embodiment of the process of the invention triazinon-benzoxazinones of formula (I), wherein $R^4$ is $R^\#$, are prepared by
a) reacting an amino-benzoxazinone of formula (II-1) with a base and a compound of formula (V) to obtain a 4-substituted amino-benzoxazinone of formula (II-2); and
b) reacting the amino-benzoxazinone of formula (II) with 1,1'-carbonyldiimidazole (CDI) and a (thio)urea compound of formula (III).

Accordingly, in a further preferred embodiment of the process of the invention triazinon-benzoxazinones of formula (I), wherein $R^4$ is $R^\#$, are prepared by
a) reacting a NH-benzoxazinone of formula (II-1) with a base and a compound of formula (V) to obtain a 4-substituted amino-benzoxazinone of formula (II-2); and
b) reacting the 4-substituted amino-benzoxazinone of formula (II-2) with 1,1'-carbonyldiimidazole (CDI) and a (thio)urea compound of formula (III).

The NH-benzoxazinones of formula (II-1) (corresponding to amino-benzoxazinones of formula (II) wherein $R^4$ is H)

can be prepared by reacting dinitro compounds of formula (VI-1) with a reducing agent to give diamino compounds of formula (VII) and subsequently treating the diamino compounds of formula (VII) with an acid:

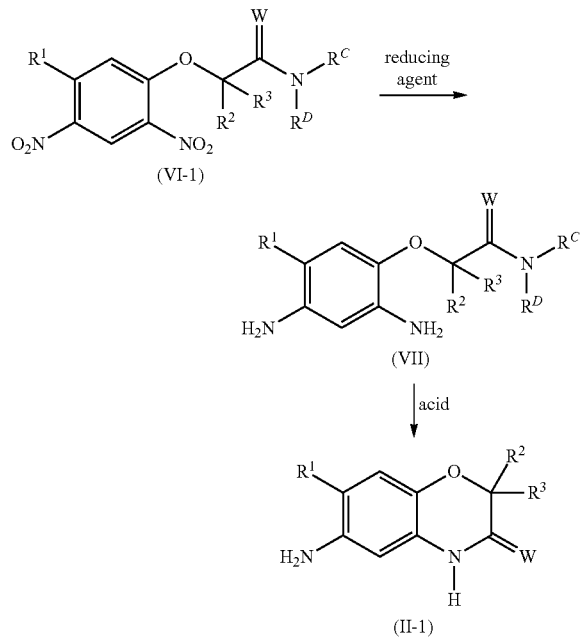

wherein
$R^C$, $R^D$ are independently of each other $C_1$-$C_6$-alkyl, $C_2$-$C_6$-alkenyl, $C_2$-$C_6$-alkynyl, $C_1$-$C_6$-haloalkyl, $C_1$-$C_6$-cyanoalkyl, $C_1$-$C_6$-nitroalkyl, $C_1$-$C_6$-hydroxyalkyl, $C_1$-$C_6$-alkoxy-$C_1$-$C_6$-alkyl, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, $C_3$-$C_6$-cycloalkyl, phenyl or benzyl, wherein the phenyl and the benzyl ring are independently of one another unsubstituted or substituted by 1 to 5 substituents selected from the group consisting of halogen, $NO_2$, $C_1$-$C_6$-alkyl or $C_1$-$C_6$-alkoxy, or $R^C$ and $R^D$ together with the N atom which they are attached to, represent a saturated or aromatic 3- to 6-membered ring, optionally containing 1 to 3 additional heteroatoms from the group O, S and N, with the ring optionally being substituted with 1 to 3 $C_1$-$C_6$-alkyl substituents; and $R^1$, $R^2$, $R^3$ and W are defined as in formula (II) above.

Accordingly, in a further preferred embodiment of the process of the invention the triazinon-benzoxazinones of formula (I), wherein $R^4$ is H, are prepared by a) reacting a dinitro compound of formula (VI-1) with a reducing agent to obtain a diamino compound of formula (VII);

b) treating the diamino compound of formula (VII) with an acid to obtain an NH-benzoxazinone of formula (II-1);

c) reacting the amino-benzoxazinone of formula (II) with 1,1'-carbonyldiimidazole (CDI) and a (thio)urea compound of formula (III).

Accordingly, in a further preferred embodiment of the process of the invention the triazinon-benzoxazinones of formula (I), wherein $R^4$ is $R^\#$, are prepared by a) reacting a dinitro compound of formula (VI-1) with a reducing agent to obtain a diamino compound of formula (VII);

b) treating the diamino compound of formula (VII) with an acid to obtain an NH-benzoxazinone of formula (II-1);

c) reacting the NH-benzoxazinone of formula (II-1) with a base and a compound of formula (V) to obtain a 4-substituted amino-benzoxazinone of formula (II-2); and d) reacting the 4-substituted amino-benzoxazinone of formula (II-2) with 1,1'-carbonyldiimidazole (CDI) and a (thio)urea compound of formula (III).

Accordingly, in a further preferred embodiment of the process of the invention the triazinon-benzoxazinones of formula (I) are prepared by a) reacting a dinitro compound of formula (VI-1) with a reducing agent to obtain a diamino compound of formula (VII);

b) treating the diamino compound of formula (VII) with an acid to obtain an NH-benzoxazinone of formula (II-1);

c) optionally reacting the NH-benzoxazinone of formula (II-1) with a base and a compound of formula (V) to obtain a 4-substituted amino-benzoxazinone of formula (II-2); and d) reacting the amino-benzoxazinone of formula (II) with 1,1'-carbonyldiimidazole (CDI) and a (thio)urea compound of formula (III).

The dinitro compounds of formula (VI-1) can be obtained by reacting haloacetamides of formula (VIII) with phenols of formula (IX) in the presence of a base to give aryloxyacetamides of formula (VI) and, if RA and/or RB in formula (VI) are H, subsequently treating the aryloxyacetamides of formula (VI) with $HNO_3/H_2SO_4$:

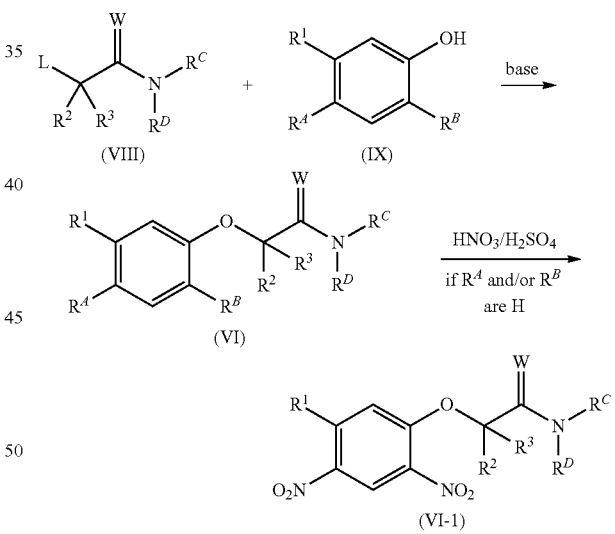

wherein
$R^A$, $R^B$ are independently H or $NO_2$;
L is halogen;
$R^1$, $R^2$, $R^3$ and W are defined as in formula (II) above; and
$R^C$ and $R^D$ are defined as above.

The phenol of formula (IX) that is converted into the aryloxyacetamide of formula (VI) can also be used in the form of a salt, for example in form of its alkali metal or alkaline metal salt, preferably in the form of its sodium, potassium, magnesium or calcium salt. If a salt of the phenol of formula (IX) is used, the addition of a base is not necessary.

Accordingly, in a further preferred embodiment of the process of the invention the triazinon-benzoxazinones of formula (I), wherein $R^4$ is H, are prepared by a) reacting an haloacetamide of formula (VIII) with a phenol of formula (IX) in the presence of a base to obtain an aryloxyacetamide of formula (VI);
b) if $R^A$ and/or $R^B$ in formula (VI) are H:
reacting the aryloxyacetamide of formula (VI) with $HNO_3$/$H_2SO_4$ to obtain a dinitro compound of formula (VI-1);
c) reacting the dinitro compound of formula (VI-1) with a reducing agent to obtain a diamino compound of formula (VII);
d) treating the diamino compound of formula (VII) with an acid to obtain an NH-benzoxazinone of formula (II-1); and
e) reacting the NH-benzoxazinone of formula (II-1) with 1,1'-carbonyldiimidazole (CDI) and a (thio)urea compound of formula (III).

Accordingly, in a further preferred embodiment of the process of the invention the triazinon-benzoxazinones of formula (I), wherein $R^4$ is $R^\#$ are prepared by a) reacting an haloacetamide of formula (VIII) with a phenol of formula (IX) in the presence of a base to obtain an aryloxyacetamide of formula (VI);
b) if $R^A$ and/or $R^B$ in formula (VI) are H:
reacting the aryloxyacetamide of formula (VI) with $HNO_3$/$H_2SO_4$ to obtain a dinitro compound of formula (VI-1);
c) reacting the dinitro compound of formula (VI-1) with a reducing agent to obtain a diamino compound of formula (VII);
d) treating the diamino compound of formula (VII) with an acid to obtain an NH-benzoxazinone of formula (II-1);
e) reacting the NH-benzoxazinone of formula (II-1) with a base and a compound of formula (V) to obtain a 4-substituted amino-benzoxazinone of formula (II-2); and
f) reacting the 4-substituted amino-benzoxazinone of formula (II-2) with 1,1'-carbonyldiimidazole (CDI) and a (thio)urea compound of formula (III).

Accordingly, in a further preferred embodiment of the process of the invention the triazinon-benzoxazinones of formula (I) are prepared by a) reacting an haloacetamide of formula (VIII) with a phenol of formula (IX) in the presence of a base to obtain an aryloxyacetamide of formula (VI);
b) if $R^A$ and/or $R^B$ in formula (VI) are H:
reacting the aryloxyacetamide of formula (VI) with $HNO_3$/$H_2SO_4$ to obtain a dinitro compound of formula (VI-1);
c) reacting the dinitro compound of formula (VI-1) with a reducing agent to obtain a diamino compound of formula (VII);
d) treating the diamino compound of formula (VII) with an acid to obtain an NH-benzoxazinone of formula (II-1);
e) optionally reacting the NH-benzoxazinone of formula (II-1) with a base and a compound of formula (V) to obtain a 4-substituted amino-benzoxazinone of formula (II-2); and
f) reacting the amino-benzoxazinone of formula (II) with 1,1'-carbonyldiimidazole (CDI) and a (thio)urea compound of formula (III).

With respect to the variables within the compounds of formulae (II-1), (II-2), (V), (VI), (VI-1), (VII), (VIII) or (IX), the particularly preferred embodiments of the compounds of formulae (II-1), (II-2), (V), (VI), (VI-1), (VII), (VIII) or (IX) correspond, either independently of one another or in combination with one another, to those of the variables of $R^1$, $R^2$, $R^3$ and W of formulae (I), (II) or (III), or have, either independently of one another or in combination with one another, the following meanings:

$R^C$ and $R^D$ preferably are independently of each other $C_1$-$C_6$-alkyl, $C_1$-$C_6$-cyanoalkyl, $C_1$-$C_6$-hydroxyalkyl, $C_1$-$C_6$-alkoxy-$C_1$-$C_6$-alkyl, $C_3$-$C_6$-cycloalkyl, phenyl or benzyl,
wherein the phenyl and the benzyl ring are independently of one another unsubstituted or substituted by 1 to 3 substituents selected from the group consisting of halogen, $C_1$-$C_6$-alkyl or $C_1$-$C_6$-alkoxy,
or $R^C$ and $R^D$ together with the N atom which they are attached to, represent a saturated or aromatic 5- to 6-membered ring, optionally containing 1 additional heteroatom from the group O and N, with the ring optionally being substituted with 1 to 2 $C_1$-$C_6$-alkyl substituents;
particularly preferred are independently of each other $C_1$-$C_4$-alkyl, $C_1$-$C_4$-hydroxyalkyl, $C_1$-$C_6$-alkoxy-$C_1$-$C_4$-alkyl or benzyl,
wherein the benzyl ring is unsubstituted or substituted by 1 to 3 substituents selected from the group consisting of halogen, $C_1$-$C_4$-alkyl or $C_1$-$C_4$-alkoxy, especially preferred the benzyl ring is unsubstituted,
or $R^C$ and $R^D$ together with the N atom which they are attached to, represent a saturated 5- to 6-membered ring, optionally containing 1 additional oxygen atom, with the ring optionally being substituted with 1 to 2 $C_1$-$C_6$-alkyl substituents;

L is preferably Cl, Br or I, particularly preferred Cl or Br, especially preferred Br;

$R^\#$ is preferably $C_3$-$C_6$-alkynyl or $C_3$-$C_6$-haloalkynyl, more preferably $C_3$-alkynyl or $C_3$-haloalkynyl, particularly preferred $CH_2C{\equiv}CH$, $CH_2C{\equiv}CCl$ or $CH_2C{\equiv}CBr$;
is also preferably $C_3$-$C_6$-alkynyl or $C_3$-$C_6$-cycloalkyl-$C_1$-$C_6$-alkyl, particularly preferred propargyl or cyclopropylmethyl;
is also preferably $C_3$-$C_6$-alkynyl, more preferably $C_3$-alkynyl; particularly preferred $CH_2C{\equiv}CH$;
is also preferably $C_3$-$C_6$-haloalkynyl, more preferably $C_3$-haloalkynyl, particularly preferred $CH_2C{\equiv}CCl$ or $CH_2C{\equiv}CBr$;

$L^\#$ is preferably halogen or $OS(O_2)R^7$,
wherein $R^7$ is $C_1$-$C_6$-alkyl, phenyl or phenyl-$C_1$-$C_6$-alkyl, wherein each phenyl ring independently of one another is unsubstituted or substituted by 1 to 3 $C_1$-$C_6$-alkyl substituents;
is particularly preferred halogen or $OS(O_2)R^7$,
wherein $R^7$ is $C_1$-$C_6$-alkyl or phenyl, wherein the phenyl ring is unsubstituted or substituted by 1 to 3 $C_1$-$C_6$-alkyl substituents;
is especially preferred Cl, Br, $OS(O)_2CH_3$ or $OS(O)_2(C_6H_4)CH_3$.

The invention is illustrated by the following examples without being limited thereto or thereby.

EXAMPLES

The yields of the triazinon-benzoxazinones of formula (I) were, unless stated otherwise, determined by means of quantitative HPLC:
Method A
Sample Preparation:
The samples of the products to be determined were weighed into a 100 ml standard flask which was made up to 100 ml with acetonitril.

Chromatographic Conditions:
  Column: Zorbax Eclipse XDB-C18 1.8 μm 50×4.6 mm from Agilent®
  Wavelength: 210 nm
  Eluent: gradient of A (0.1% by volume of $H_3PO_4$ in $H_2O$) and B (0.1% by volume of $H_3PO_4$ in acetonitrile); starting with 2% B, then B rising from 2% to 30% within 2 min, then B rising from 30% to 100% within 6 min, then 2 min 100% B, then back to 2% within 0.1 min.
  Flow rate: 1.4 ml/min
  Pressure: approx. 210 bar
Calibration:
  The calibration was effected with external standard. To establish the standard, a total of 5 samples of the pure substances were weighed in the following concentrations (precision+/−0.1 mg): approx. 0.02 g/l, approx. 0.04 g/l, approx. 0.06 g/l, approx. 0.08 g/l, approx. 0.10 g/l. With the aid of a suitable PC program, a calibration line was established. For the substances detailed above, this was a linear function. Standard deviation, correlation coefficient and straight-line equation were calculated. For each of the components, their concentration can thus be determined based on the particular external standard.

1. Preparation of Triazinon-Benzoxazinones of Formula (I)

Example 1.1 to 1.2

1,5-Dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione

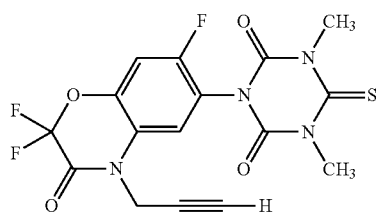 [SMILES: C#CCN1C(=O)C(F)(F)Oc2cc(F)c(-n3c(=O)n(C)c(=S)n(C)c3=O)cc21]

Example 1.1

374.6 g (2.2647 mol) 1,1'-carbonyldiimidazole (98%), 76.4 g (0.7549 mol) triethyl-amine and 2437 g ethyl acetate were initially charged at 20° C. in a stirred vessel. 200 g (0.7549 mol) 6-amino-2,2,7-trifluoro-4-prop-2-ynyl-4H-benzo[1,4]oxazin-3-one (96.7%) were added in portions. The reaction mixture was heated to 55° C. At this temperature 95.4 g (0.9064 mol) N,N'-dimethylthiourea (99%) were added. The reaction mixture was stirred at 75-77° C. for 25 hours and then poured to a mixture of 2680 ml ice/water and 460 ml hydrochloric acid (32%). The phases were separated and the aqueous phase was extracted twice with 775 ml ethyl acetate. The combined organic phases were dried with $Na_2SO_4$ and concentrated to yield 322.9 g. The residue was dissolved in 5970 ml methanol at 65° C. 5600 ml methanol were distilled off and the remaining suspension was cooled to 0° C. The solid was filtered off and washed with 100 ml cold methanol. The wet solid was dried in a vacuum cabinet at 50° C./10 mbar over 24 hours. 271.0 g of the desired product with a purity of 99.8% (determined by quant. HPLC; HPLC-method A; $t_R$=5.9 min) were isolated. The yield (based on the amino compound used) was 86.9%.

The obtained solid showed the following spectroscopical data:
$^1$H-NMR (400 MHz, $CDCl_3$): δ (ppm)=2.39 (s, 1H), 3.80 (s, 6H), 4.75 (s, 2H), 7.18 (d, 1H), 7.27 (d, 1H).
$^{13}$C-NMR (125 MHz, $CDCl_3$): δ (ppm)=177.37 (s); 154.59 (s); 153.05 (s); 146.68 (s); 140.14 (s); 122.66 (s); 118.40 (s); 117.20 (d); 112.19 (s); 107.34 (d), 75.07 (d); 74.93 (s); 36.86 (q); 32.18 (t).

Example 1.2

496.2 g (3.0 mol) 1,1'-carbonyldiimidazole (98%), 102.2 g (1.0 mol) triethylamine (99%) and 3236 g ethyl acetate were initially charged at 20° C. in a stirred vessel. 264.7 g (1.0 mol) 6-amino-2,2,7-trifluoro-4-prop-2-ynyl-4H-benzo[1,4]oxazin-3-one 96.7%) were added in portions. The reaction mixture was heated to 55° C. At this temperature 126.3 g (1.2 mol) N,N'-dimethylthiourea (99%) were added. The reaction mixture was stirred at 77-79° C. (reflux) for 25 hours and then poured to a mixture of 3526 g ice/water and 490 g hydrochloric acid (32%). The mixture was stirred for 30 minutes. The phases were separated and the aqueous phase was extracted twice with 890 g ethyl acetate. The combined organic phases were washed with 1500 g water and dried with $Na_2SO_4$. 3240 g ethyl acetate were distilled off. Thereafter 3555 g methanol was added in portions and 4778 g ethyl acetate/methanol were simultaneously distilled off (final concentration of ethyl acetate was below 0.5%). The remaining suspension was cooled to 0° C. The solid was filtered off and washed twice with 119 g cold methanol. The wet solid was dried in a vacuum cabinet at 50° C./10 mbar over 24 hours. 344.5 g of the desired product with a purity of 98% (determined by quant. HPLC; HPLC-method A; $t_R$=5.9 min) were isolated. The yield (based on the amino compound used) was 81.9%.

2. Preparation of Amino-Benzoxazinones of Formula (II)

2.1 Preparation of 4-Substituted Amino-Benzoxazinones of Formula (II-2)

Examples 2.1.1 to 2.1.5

6-Amino-2,2,7-trifluoro-4-prop-2-ynyl-4H-benzo[1,4]oxazin-3-one

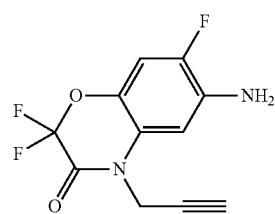 [SMILES: C#CCN1C(=O)C(F)(F)Oc2cc(F)c(N)cc21]

Example 2.1.1

61.0 g (0.2678 mol) 6-amino-2,2,7-trifluoro-4H-benzo[1,4]oxazin-3-one, 360 g ethyl acetate and 38.9 g (0.2815 mol) potassium carbonate were initially charged at 25° C. in a stirred vessel. 43.8 g (0.2945 mol) propargyl bromide (80% w/w in toluene) were added at 25-30° C. within 15 minutes. Thereafter the reaction mixture was stirred at 78° C. for 8 hours and then cooled to 25° C. The precipitated salt was filtered off and washed with 360 g of ethyl acetate. The combined ethyl acetate solutions were washed with 200 g hydrochloric acid (1%) and twice with 200 g water. The organic phase was dried by azeotropic distillation (ca. 600 g distillate). The remaining solution (158.5 g) comprised 40.3% by weight of the desired product (HPLC analysis with external standard). The yield (based on the amino compound used) was 93.1%.

From a small quantity of the solution the solvent was completely distilled off at reduced pressure. The remaining residue was recrystallized from methanol and dried. The obtained crystals (melting point: 239.2° C.) showed the following spectroscopical data:

1H-NMR (500 MHz, DMSO-d6): δ (ppm)=3.45 (s, 1H), 4.74 (s, 2H), 5.42 (s, 2H), 6.85 (d, 1H), 7.26 (d, 1H)

Example 2.1.2

219.1 g (1.0 mol) 6-amino-2,2,7-trifluoro-4H-benzo[1,4] oxazin-3-one, 1100 g dimethylformamide and 145.5 g (1.053 mol) potassium carbonate were initially charged at 25° C. in a stirred vessel. 163.2 g (1.1 mol) propargyl bromide (80% w/w in toluene) were added at 25-30° C. within 30 minutes. Thereafter the reaction mixture was stirred at 60° C. for 2 hours and then cooled to 25° C. The precipitated salt was filtered off and washed with 3300 g of ethyl acetate. The combined organic solutions were washed with 750 g water and with 750 g sodium sulfate solution (5%). The combined inorganic phases were extracted three times with 550 g ethyl acetate. All organic phases were combined and dried by aceotropic distillation. The remaining solution (635.3 g) comprised 40.05% by weight of the desired product (HPLC analysis with external standard). The yield (based on the amino compound used) was 97.8%.

Example 2.1.3

0.8 g (0.00348 mol) 6-amino-2,2,7-trifluoro-4H-benzo[1,4]oxazin-3-one (purity: 94.9%) were dissolved in 19.76 g ethyl acetate at 20° C. 0,075 g ethyltrimethylammoniumiodide and 0.284 g (0.00205 mol) potassium carbonate were added. Then 0.463 g (0.00435 mol) propargyl chloride (70% in toluene) were added. The mixture was heated to reflux (73-77° C.) over 10 h. Reaction mixture was cooled to 25° C. and 20 g water was added under stirring. Phases were separated. The organic phase was evaporated to dryness at 45° C./4 mbar. 0.9 g solid with a purity of 95.0% (determined by quantitative HPLC) were isolated (yield: 95.9%).

Example 2.1.4

0.8 g (0.00348 mol) 6-amino-2,2,7-trifluoro-4H-benzo[1,4]oxazin-3-one (purity: 94.9%) were dissolved in 20 g ethyl acetate at 20° C. 0.505 g (0.00365 mol) potassium carbonate and 0.614 g (0.00435 mol) propargyl mesylate (95%) were added as solid. The mixture was heated to reflux (77° C.) over 3 h. Reaction mixture was cooled to 25° C. and 20 g water was added under stirring. Phases were separated. The organic phase was evaporated to dryness at 45° C./4 mbar. 1.0 g solid with a purity of 88.1% (determined by quantitative HPLC) were isolated (yield: 98.9%).

Example 2.1.5

13.22 g (0.06 mol) 6-amino-2,2,7-trifluoro-4H-benzo[1,4] oxazin-3-one (purity: 99%) were dissolved in 48 g DMF at 20° C. 10.67 g (0.077 mol) potassium carbonate and 7.98 g (0.075 mol) propargyl chloride (70% in toluene) were added. The mixture was stirred at 72° C. for 2 h. Reaction mixture was cooled to 3° C. and 120 g water were added under stirring over a period of 2 h at 3-5° C. Suspension was stirred for 3 h at 0-5° C. The solid was filtered off and washed with water. The wet solid was dried in a vacuum cabinet at 50° C./3 mbar over 17 hours. 14.8 g of a light brown solid with a purity of 99.3% (determined by quant. HPLC) were isolated (yield: 95.6%).

2.2 Preparation of NH-Benzoxazinones of Formula (II-1)

Example 2.2.1

Synthesis of 6-amino-2,2,7-trifluoro-4H-benzo-[1,4] oxazin-3-one from 2,2-difluoro-2(2,4-dinitro-5-fluoro-phenoxy)-N,N-dimethyl-acetamide

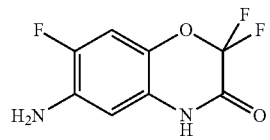

To a solution of 2,2-difluoro-2-(2,4-dinitro-5-fluoro-phenoxy)-N,N-dimethyl-acetamide (60.0 g, 186 mmol) in toluene (432 g) was added Pd on charcoal (5% Pd, 50% water content, 1.1 mmol). Thereafter MeOH (492 g) was added and the mixture was stirred under an atmosphere of hydrogen (over pressure 0.1 bar) at 45° C. for 2 h. After completion of the reaction the pressure was released, concentrated HCl (36.5%, 22 g, 220 mmol) added and the reaction mixture heated to reflux for further 1 h. The catalyst was filtered off, the pH adjusted with NaOH to 9 and the MeOH distilled off under reduced pressure. After addition of water (200 g) and stirring for 1 h the precipitate was filtered off, washed twice with water (100 g) and dried at 50° C. under reduced pressure. The product was obtained as a tan solid (38.9 g, 90% pure by NMR, 160 mmol, 86% yield).

$^1$H NMR (DMSO-d$_6$, 500 MHz): δ (ppm)=11.9 (bs, 1H); 7.15 (d, J=11.0 Hz, 1H); 6.55 (d, J=8.5 Hz, 1H); 5.28 (bs, 2H).

$^{13}$C NMR (DMSO-d$_6$, 125 MHz): δ (ppm)=153.7 (t, J=38 Hz); 146.1 (d, J=235 Hz); 133.9 (d, J=15 Hz); 127.3 (d, J=11 Hz); 120.9 (d, J=3 Hz); 113.1 (t, J=260 Hz); 104.9 (d, J=24 Hz); 102.4 (d, J=5 Hz).

3. Preparation of Diamino Compounds of Formula (VII)

Example 3.1

Synthesis of 2,2-difluoro-2-(2,4-diamino-5-fluoro-phenoxy)-N,N-dimethyl-acetamide

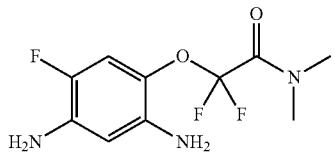

To a solution of 2,2-difluoro-2-(2,4-dinitro-5-fluoro-phenoxy)-N,N-dimethyl-acetamide (22.0 g, 68.1 mmol) in toluene (200 g) obtained according to example 4.1 alternative 2 Pd/C (10% Pd, dry catalyst, 0.7 g, 0.7 mmol) was added. Thereafter, MeOH (80 g) was added and the mixture was stirred under an atmosphere of hydrogen (pressure of 0.1 bar) at 45° C. for 90 min. After completion of the reaction the pressure was released, the catalyst was filtered off and the filtrate was evaporated to dryness. The product (17.3 g, 84% pure by NMR, 55.2 mmol, 81% yield) was obtained as an off-white solid. If desired, the purity can be increased by chromatography (SiO$_2$, cyclohexane/EtOAc mixtures).

$^1$H NMR (DMSO-d$_6$, 500 MHz): δ (ppm)=6.79 (d, J=11.0 Hz, 1H); 6.16 (d, J=8.5 Hz, 1H); 4.95 (bs, 2H); 4.60 (bs, 2H); 3.19 (s, 3H); 2.96 (bs, 3H).

$^{13}$C NMR (DMSO-d$_6$, 125 MHz): δ (ppm)=158.3 (t, J=35 Hz); 141.7 (d, J=278 Hz); 137.6; 134.9 (d, J=14 Hz); 123.9 (d, J=9 Hz); 115.8 (t, J=272 Hz); 109.2 (d, J=22 Hz); 102.0 (d, J=4 Hz); 36.9; 36.2.

Example 3.2

Synthesis of 2,2-difluoro-2-(2,4-diamino-5-fluoro-phenoxy)-N,N-diethyl-acetamide

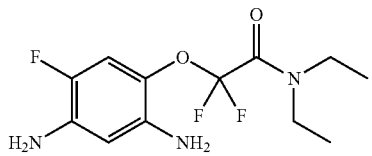

A solution of 2,2-difluoro-2-(2,4-dinitro-5-fluoro-phenoxy)-N,N-diethyl-acetamide (13.5 g, 38.4 mmol) obtained according to example 4.1 alternative 2, and Pd/C (10% Pd, dry catalyst, 2.0 g, 1.9 mmol) in MeOH (395) was stirred under an atmosphere of hydrogen (pressure of 0.1 bar) at 50° C. for 2 h. After completion of the reaction the pressure was released, the catalyst was filtered off and the filtrate was evaporated to dryness. The product was purified by column chromatography (SiO$_2$, cyclohexane/EtOAc mixtures). The product was obtained as an off-white solid (11.0 g, 88% pure by NMR, 33.2 mmol, 86% yield).

$^1$H NMR (CDCl$_3$, 500 MHz): δ (ppm)=6.85 (d, J=11.0 Hz, 1H); 6.19 (d, J=8.5 Hz, 1H); 3.71 (bs, 4H); 3.58 (q, J=7.0 Hz, 2H); 3.45 (q, J=7.0 Hz, 2H); 1.25 (t, J=7.0 Hz, 3H); 1.19 (t, J=7.0 Hz, 3H).

$^{13}$C NMR (CDCl$_3$, 125 MHz): δ (ppm)=158.8 (t, J=35 Hz); 143.7 (d, J=231 Hz); 136.5; 133.5 (d, J=14 Hz); 126.9 (d, J=9 Hz); 116.1 (t, J=273 Hz); 110.3 (d, J=23 Hz); 103.8 (d, J=3 Hz); 42.4; 41.6; 14.1; 12.6.

4. Preparation of Dinitro Compounds of Formula (VI-1)

Example 4.1

Synthesis of 2,2-difluoro-2-(2,4-dinitro-5-fluoro-phenoxy)-N,N-dimethyl-acetamide

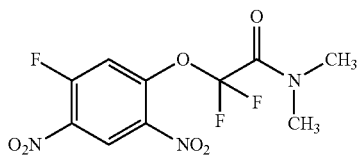 [SMILES: CN(C)C(=O)C(F)(F)Oc1cc(F)c([N+](=O)[O-])cc1[N+](=O)[O-]]

Alternative 1:

To a mixture of H$_2$SO$_4$ (98%, 34.5 g, 345 mmol) and HNO$_3$ (100%, 11.0 g, 175 mmol) at room temperature was added 2,2-difluoro-2-(3-fluoro-phenoxy)-N,N-dimethyl-acetamide (8.7 g, 37 mmol). The temperature rose to 40° C. and was kept at that temperature for further 3 h. The mixture was then poured on 100 g of ice-water. The precipitate was taken up in 50 g of toluene and the aqueous phase was extracted with 25 g of toluene. The combined org. phases were washed with saturated NaHCO$_3$ solution and water. The crude product (11.5 g, 82% purity by quant. HPLC, 29 mmol, 78% yield) was obtained after removal of all volatiles as a yellowish solid. Analytically pure material the crude material could be obtained after recrystallisation from cyclohexane/EtOAc (80:20).

Alternative 2:

A solution of 61.5 g HNO$_3$ (100%, 0.976 mol) and 433.7 g H$_2$SO$_4$ (96%, 4.245 mol) was prepared at 0-20° C. by addition of HNO$_3$ to the sulfuric acid (quantity of mixed acid: 495.2 g). 100 g 2,2-difluoro-2-(3-fluoro-phenoxy)-N,N-dimethyl-acetamide (99%, 0.425 mol) was filled into the reaction vessel at 0° C. 236.9 g of the mixed acid (portion 1) was added at a rate to keep the temperature between 0 and 10° C.

258.3 of the mixed acid (portion 2) was dosed at 40° C. Upon complete addition the mixture was kept at 40° C. for another 9 h. Then, it was cooled to 25° C. and poured to a mixture of 1000 g ice water and 500 ml toluene. Reactor was rinsed with 100 g water and 50 g toluene. The phases were separated at 20° C. The aqueous layer was extracted with 240 g toluene and then discarded. The combined organic layers were washed 4 times with 400 g water in each case (final pH-value of the organic phase: 3). The water in the remaining organic phase was removed by distilling off toluene/water at reduced pressure. The product was obtained as a solution in toluene: 541.3 g (concentration of the dinitro compound by quant. HPLC: 22.3%; yield: 88.1%).

$^1$H NMR (CDCl$_3$, 400 MHz): δ (ppm)=8.82 (d, J=7.5 Hz, 1H); 7.52 (d, J=11.0 Hz, 1H); 3.26 (s, 3H); 3.11 (s, 3H).

$^{13}$C NMR (CDCl$_3$, 100 MHz): δ (ppm)=157.1 (d, J=276 Hz); 156.7 (d, J=34 Hz); 147.6 (td, J=3 Hz, J=11 Hz); 136.9; 132.9 (d, J=9 Hz); 124.2; 115.3 (t, J=281 Hz); 111.7 (td, J=3 Hz, J=26 Hz); 36.8; 36.7.

Melting point: 66° C.

Example 4.2

Synthesis of 2,2-difluoro-2-(2,4-dinitro-5-fluoro-phenoxy)-N,N-diethyl-acetamide

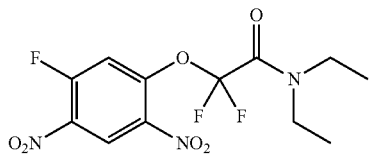 [SMILES: CCN(CC)C(=O)C(F)(F)Oc1cc(F)c([N+](=O)[O-])cc1[N+](=O)[O-]]

To a mixture of H$_2$SO$_4$ (98%, 261 g, 2.61 mol) and HNO$_3$ (100%, 107 g, 1.7 mol) at 0° C. was added 2,2-difluoro-2-(3-fluoro-phenoxy)-N,N-diethyl-acetamide (34 g, 130 mmol) with cooling. The mixture was then warmed to r.t. and stirred for further 3 h. Then, the mixture was poured on 750 g ice-water. TBME (250 mL) was added and the aqueous phase was extracted with TBME (200 mL). The combined organic phases were washed with water (300 mL), saturated NaHCO$_3$ solution and brine. Drying over Na$_2$SO$_4$ and evaporation of all volatiles gave the product as a yellow solid.

$^1$H NMR (CDCl$_3$, 500 MHz): δ (ppm)=8.82 (d, J=7.5 Hz); 7.53 (d, J=11.0 Hz, 1H); 3.57 (q, J=7.0 Hz, 2H); 3.45 (q, J=7.0 Hz, 2H); 1.27 (t, J=7.0 Hz, 3H); 1.18 (t, J=7.0 Hz, 3H).

$^{13}$C NMR (CDCl$_3$, 125 MHz): δ (ppm)=157.6 (d, J=268 Hz); 156.6 (t, J=34 Hz); 148.2 (d, J=11 Hz); 137.3; 133.3 (d, J=8 Hz); 124.7; 115.8 (t, J=281 Hz); 112.3 (d, J=26 Hz); 42.3; 42.0; 14.1; 12.2.

Example 4.3

Synthesis of 2,2-difluoro-2-(2,4-dinitro-5-fluoro-phenoxy)-1-pyrrolidine-1-yl-ethanone

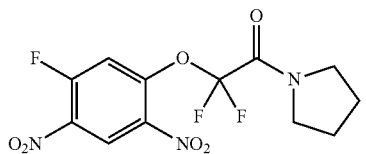 [SMILES: O=C(N1CCCC1)C(F)(F)Oc1cc(F)c([N+](=O)[O-])cc1[N+](=O)[O-]]

To a mixture of H$_2$SO$_4$ (98%, 22.0 g, 220 mmol) and HNO$_3$ (100%, 8.5 g, 135 mmol) at 0° C. was added 2,2-difluoro-2-(3-fluoro-phenoxy)-1-pyrrolidine-1-yl-ethanone (3.3 g, 12.7 mmol). The temperature rose to 10° C. and was kept at that temperature for further 16 h. The mixture was then poured on 150 g of ice-water and 80 mL of TBME. The aqueous phase was extracted with 50 mL of TBME. The combined org. phases were washed with saturated NaHCO$_3$ solution and water. The crude product (3.6 g, >98% purity by HPLC, 10.3 mmol, 81% yield) was obtained after removal of all volatiles as a yellow solid.

$^1$H NMR (CDCl$_3$, 500 MHz): δ (ppm)=8.81 (d, J=7.5 Hz, 1H); 7.54 (d, J=11.0 Hz, 1H); 3.72-3.78 (m, 4H); 3.54-3.59 (m, 4H); 2.02-2.09 (m, 4H); 1.92-1.98 (m, 4H).

$^{13}$C NMR (CDCl$_3$, 125 MHz): δ (ppm)=157.6 (d, J=274 Hz); 155.7 (t, J=34 Hz); 148.2 (d, J=11 Hz); 137.4; 133.3 (d, J=8 Hz); 124.7; 115.6 (t, J=280 Hz); 112.5 (d, J=32 Hz); 47.9; 47.0; 26.4; 23.5.

Melting point: 78° C.

Example 4.4

Synthesis of 2,2-difluoro-2-(2,4-dinitro-5-fluoro-phenoxy)-1-morpholine-1-yl-ethanone

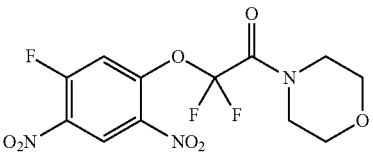 [SMILES: O=C(N1CCOCC1)C(F)(F)Oc1cc(F)c([N+](=O)[O-])cc1[N+](=O)[O-]]

To a mixture of H$_2$SO$_4$ (96%, 68.8 g, 701 mmol) and HNO$_3$ (100%, 13.3 g, 210 mmol) at 0° C. was added 2,2-difluoro-2-(3-fluoro-phenoxy)-1-morpholine-1-yl-ethanone (18.3 g, 90% pure, 60 mmol). The temperature was eventually increased to 40° C. and was kept at room temperature for 60 min. The mixture was then poured on 160 g of ice-water. and 80 g of chlorobenzene. The aqueous phase was extracted with chlorobenzene (2×40 mL). The combined org. phases were washed with saturated NaHCO$_3$ solution and water. The crude product (12.3 g, >90% purity by HPLC) was obtained after removal of all volatiles as a reddish solid. Recrystallisation from n-BuOH (150 mL) gave the product as a yellow solid.

$^1$H NMR (CDCl$_3$, 500 MHz): δ (ppm)=8.82 (d, J=7.0 Hz, 1H); 7.52 (d, J=10.5 Hz, 1H); 3.68-3.78 (m, 8H).

$^{13}$C NMR (CDCl$_3$, 125 MHz): δ (ppm)=157.5 (d, J=274 Hz); 155.8 (t, J=34 Hz); 147.6 (d, J=11 Hz); 137.2; 135.3; 124.7; 115.4 (t, J=281 Hz); 112.1 (d, J=26 Hz); 66.5; 66.4; 46.6; 43.8.

Melting point: 96° C.

5. Preparation of Aryloxyacetamides of Formula (VI)

Example 5.1

Synthesis of 2,2-difluoro-2-(5-fluoro-2-nitro-phenoxy)-N,N-dimethyl-acetamide

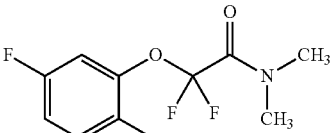

A mixture of 2-nitro-5-fluoro-phenol (3.0 g, 19.1 mmol), 2-bromo-2,2-difluoro-N,N-dimethylacetamide (3.9 g, 19.1 mmol) and Na$_2$CO$_3$ (2.1 g, 19.8 mmol) in 30 mL of DMAC was heated to 100° C. overnight. The mixture was then poured on 50 mL of H$_2$O and extracted with TBME (2×50 mL). The combined organic layers were washed with 10% NaOH (50 mL) and dried over Na$_2$SO$_4$. The crude product was obtained after evaporation of all volatiles. Purification by chromatography on silica gave the product (1.8 g, 6.4 mmol, 38% yield) as a yellow oil that solidified upon standing.

$^1$H NMR (CDCl$_3$, 500 MHz): δ (ppm)=8.04 (dd, J=5.5 Hz, J=9.0 Hz, 1H); 7.26-7.29 (m, 1H); 7.13 (dd, J=2.5 Hz, J=7.5 Hz, 1H); 3.25 (s, 3H); 3.09 (s, 3H).

$^{13}$C NMR (CDCl$_3$, 125 MHz): δ (ppm)=164.5 (d, J=258 Hz); 157.9 (t, J=34 Hz); 143.9 (d, J=11 Hz); 138.9; 127.9 (d, J=11 Hz); 115.5 (t, J=278 Hz); 113.6 (d, J=10 Hz); 110.9 (d, J=28 Hz); 37.2; 37.1.

The invention claimed is:

1. A process for manufacturing a compound of formula (I),

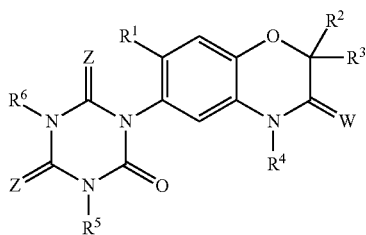

(I)

wherein
R$^1$ is H or halogen;
R$^2$ is halogen;
R$^3$ is H or halogen;
R$^4$ is H, C$_1$-C$_6$-alkyl, C$_1$-C$_6$-haloalkyl, C$_3$-C$_6$-cycloalkyl, C$_3$-C$_6$-alkenyl, C$_3$-C$_6$-haloalkenyl, C$_3$-C$_6$-alkynyl, C$_3$-C$_6$-haloalkynyl, C$_1$-C$_6$-alkoxy or C$_3$-C$_6$-cycloalkyl-C$_1$-C$_6$-alkyl;
R$^5$ is H or C$_1$-C$_6$-alkyl;
R$^6$ is H or C$_1$-C$_6$-alkyl;
W is O or S; and
Z is O or S;
wherein a compound of formula (II),

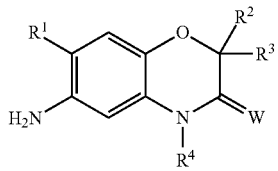

(II)

wherein R$^1$, R$^2$, R$^3$, R$^4$ and W are defined as in formula (I);
is reacted with 1,1'-carbonyldiimidazole (CDI) and a compound of formula (III),

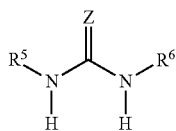

(III)

wherein R$^5$, R$^6$ and Z are defined as in formula (I).

2. The process according to claim 1, wherein R$^1$ and R$^3$ are halogen.

3. The process according to claim 1, wherein
R$^2$ is F;
R$^5$ is C$_1$-C$_6$-alkyl;
R$^6$ is C$_1$-C$_6$-alkyl;
W is O; and
Z is S.

4. The process according to claim 1, wherein R$^4$ is C$_3$-C$_6$-alkynyl.

5. The process according to claim 1, wherein the aminobenzoxazinone formula (II) is reacted with CDI and a compound of formula (III) in the presence of a base.

6. The process according to claim 1, wherein the compound formula (II) is prepared by
a) reacting a dinitro compound of formula (VI-1)

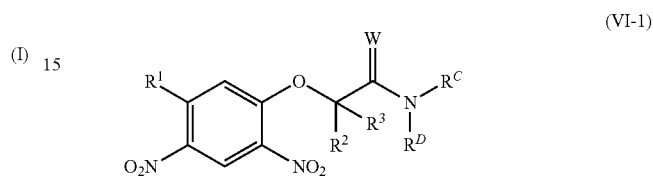

(VI-1)

wherein R$^1$, R$^2$, R$^3$ and W are defined as in claim 1; and R$^C$, R$^D$ are independently of each other C$_1$-C$_6$-alkyl, C$_2$-C$_6$-alkenyl, C$_2$-C$_6$-alkynyl, C$_1$-C$_6$-haloalkyl, C$_1$-C$_6$-cyanoalkyl, C$_1$-C$_6$-nitroalkyl, C$_1$-C$_6$-hydroxyalkyl, C$_1$-C$_6$-alkoxy-C$_1$-C$_6$-alkyl, amino-C$_1$-C$_6$-alkyl, (C$_1$-C$_6$-alkyl)amino-C$_1$-C$_6$-alkyl, di(C$_1$-C$_6$-alkyl)amino-C$_1$-C$_6$-alkyl, C$_3$-C$_6$-cycloalkyl, phenyl or benzyl, wherein the phenyl and the benzyl ring are independently of one another unsubstituted or substituted by 1 to 5 substituents selected from the group consisting of halogen, NO$_2$, C$_1$-C$_6$-alkyl or C$_1$-C$_6$-alkoxy,
or R$^C$ and R$^D$ together with the N atom which they are attached to, represent a saturated or aromatic 3- to 6-membered ring, optionally containing 1 to 3 additional heteroatoms from the group O, S and N, with the ring optionally being substituted with 1 to 3 C$_1$-C$_6$-alkyl substituents
with a reducing agent to obtain a diamino compound of formula (VII)

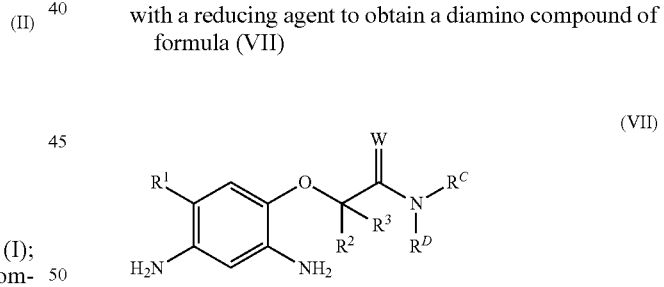

(VII)

wherein R$^1$, R$^2$, R$^3$ and W are defined as in claim 1, and R$^C$ and R$^D$ are defined as above;
b) treating the diamino compound of formula (VII) with an acid to obtain an NH-benzoxazinone of formula (II-1);

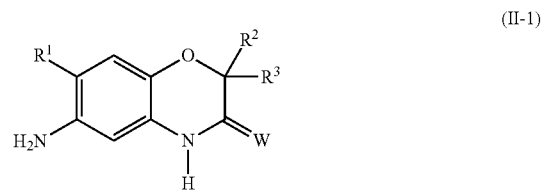

(II-1)

wherein R$^1$, R$^2$, R$^3$ and W are defined as in claim 1;

c) optionally reacting the NH-benzoxazinone of formula (II-1) with a base and a compound of formula (V)

$$R^\#\text{-}L^\# \quad\quad (V)$$

wherein
- $R^\#$ is $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;
- $L^\#$ is halogen or $OS(O)_2R^7$;
- $R^7$ is $C_1$-$C_6$-alkyl, $C_1$-$C_6$-haloalkyl, $C_1$-$C_6$-nitroalkyl, $C_1$-$C_6$-alkoxy-$C_1$-$C_6$-alkyl, $C_3$-$C_6$-cycloalkyl, phenyl or phenyl-$C_1$-$C_6$-alkyl, wherein each phenyl ring independently of one another is unsubstituted or substituted by 1 to 5 substituents selected from the group consisting of halogen, CN, $NO_2$, $C_1$-$C_6$-alkyl, $C_1$-$C_6$-haloalkyl or $C_1$-$C_6$-alkoxy;

to obtain a 4-substituted amino-benzoxazinone of formula (II-2).

7. The process according to claim 2, wherein
$R^2$ is F;
$R^5$ is $C_1$-$C_6$-alkyl;
$R^6$ is $C_1$-$C_6$-alkyl;
W is O; and
Z is S.

8. The process according to claim 7, wherein $R^4$ is $C_3$-$C_6$-alkynyl.

9. The process according to claim 8, wherein the amino-benzoxazinone formula (II) is reacted with CDI and a compound of formula (III) in the presence of a base.

10. The process according to claim 9, wherein the amino-benzoxazinones of formula (II) are prepared by
a) reacting a dinitro compound of formula (VI-1)

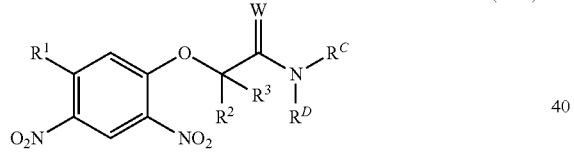
(VI-1)

wherein
- $R^1$, $R^2$, $R^3$ and W are defined as in claim 1; and
- $R^C$, $R^D$ are independently of each other $C_1$-$C_6$-alkyl, $C_2$-$C_6$-alkenyl, $C_2$-$C_6$-alkynyl, $C_1$-$C_6$-haloalkyl, $C_1$-$C_6$-cyanoalkyl, $C_1$-$C_6$-nitroalkyl, $C_1$-$C_6$-hydroxyalkyl, $C_1$-$C_6$-alkoxy-$C_1$-$C_6$-alkyl, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, $C_3$-$C_6$-cycloalkyl, phenyl or benzyl, wherein the phenyl and the benzyl ring are independently of one another unsubstituted or substituted by 1 to 5 substituents selected from the group consisting of halogen, $NO_2$, $C_1$-$C_6$-alkyl or $C_1$-$C_6$-alkoxy, or $R^C$ and $R^D$ together with the N atom which they are attached to, represent a saturated or aromatic 3- to 6-membered ring, optionally containing 1 to 3 additional heteroatoms from the group O, S and N, with the ring optionally being substituted with 1 to 3 $C_1$-$C_6$-alkyl substituents with a reducing agent to obtain a diamino compound of formula (VII)

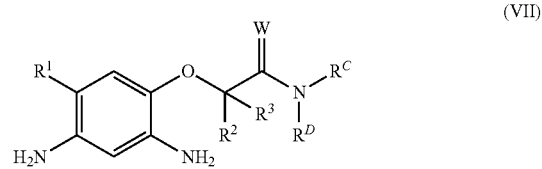
(VII)

wherein $R^1$, $R^2$, $R^3$ and W are defined as in claim 1, and $R^C$ and $R^D$ are defined as above;

b) treating the diamino compound of formula (VII) with an acid to obtain an NH-benzoxazinone of formula (II-1);

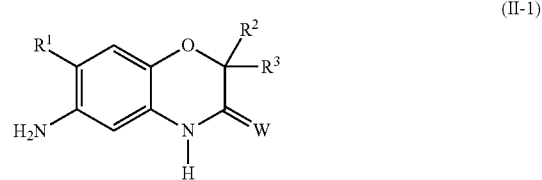
(II-1)

wherein $R^1$, $R^2$, $R^3$ and W are defined as in claim 1;

c) optionally reacting the NH-benzoxazinone of formula (II-1) with a base and a compound of formula (V)

$$R^\#\text{-}L^\# \quad\quad (V)$$

wherein
- $R^\#$ is $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;
- $L^\#$ is halogen or $OS(O)_2R^7$;
- $R^7$ is $C_1$-$C_6$-alkyl, $C_1$-$C_6$-haloalkyl, $C_1$-$C_6$-nitroalkyl, $C_1$-$C_6$-alkoxy-$C_1$-$C_6$-alkyl, $C_3$-$C_6$-cycloalkyl, phenyl or phenyl-$C_1$-$C_6$-alkyl, wherein each phenyl ring independently of one another is unsubstituted or substituted by 1 to 5 substituents selected from the group consisting of halogen, CN, $NO_2$, $C_1$-$C_6$-alkyl, $C_1$-$C_6$-haloalkyl or $C_1$-$C_6$-alkoxy;

to obtain a 4-substituted amino-benzoxazinone of formula (II-2).

* * * * *